United States Patent [19]

Massardo et al.

[11] Patent Number: 4,496,771
[45] Date of Patent: Jan. 29, 1985

[54] PROCESS FOR PREPARING THE COMPOUND 1-DECYLOXY-4-[(7-OXA-4-OCTYNYL)-OXY]-BENZENE

[75] Inventors: Pietro Massardo, Milan; Franco Bettarini; Ennio Bianchini both of Novara; Paolo Piccardi, Milan, all of Italy.

[73] Assignee: Montedison S.p.A., Milan, Italy

[21] Appl. No.: 471,706

[22] Filed: Mar. 3, 1983

[30] Foreign Application Priority Data

Mar. 4, 1982 [IT] Italy ................. 19957 A/82

[51] Int. Cl.³ .................... C07C 41/16; C07C 43/205
[52] U.S. Cl. ..................... 568/651; 568/686
[58] Field of Search ................. 568/654, 686, 651,

[56] References Cited

U.S. PATENT DOCUMENTS

| | | | |
|---|---|---|---|
| 3,162,653 | 12/1964 | Pullen et al. | 568/686 X |
| 3,880,935 | 4/1975 | Chodnekar et al. | 568/654 |
| 4,029,649 | 6/1977 | Karrer | 568/654 |
| 4,388,323 | 6/1983 | Massardo et al. | 568/654 X |

Primary Examiner—Bernard Helfin

[57] ABSTRACT

There is described a process for preparing the compound 1-decyloxy-4-[(7-oxa-4-octynyl)-oxy]-benzene consisting in condensing methyl-propargyl-ether with 1-bromo-3-chloro-propane and in reacting the resulting intermediate with 4-decyloxy-phenol in the presence of an alkaline hydroxide.

The process can be carried out also without purifying the intermediate obtained from the first reaction.

5 Claims, No Drawings

PROCESS FOR PREPARING THE COMPOUND 1-DECYLOXY-4-[(7-OXA-4-OCTYNYL)-OXY]-BENZENE

BACKGROUND OF THE INVENTION

European patent application No. 37,092 describes compounds endowed with a high acaricide activity, among which also the compound 1-decyloxy-4-[(7-oxa-4-octynyl)-oxy]-benzene of formula:

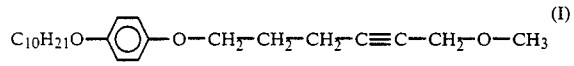
(I)

(hereinafter referred to as compound I).

In the abovesaid European patent application there are described also synthesis processes suitable for preparing the different acaricide compounds.

These processes include also the process indicated in the following scheme 1, where it is described in the specific form suitable for the synthesis of compound I.

Scheme 1

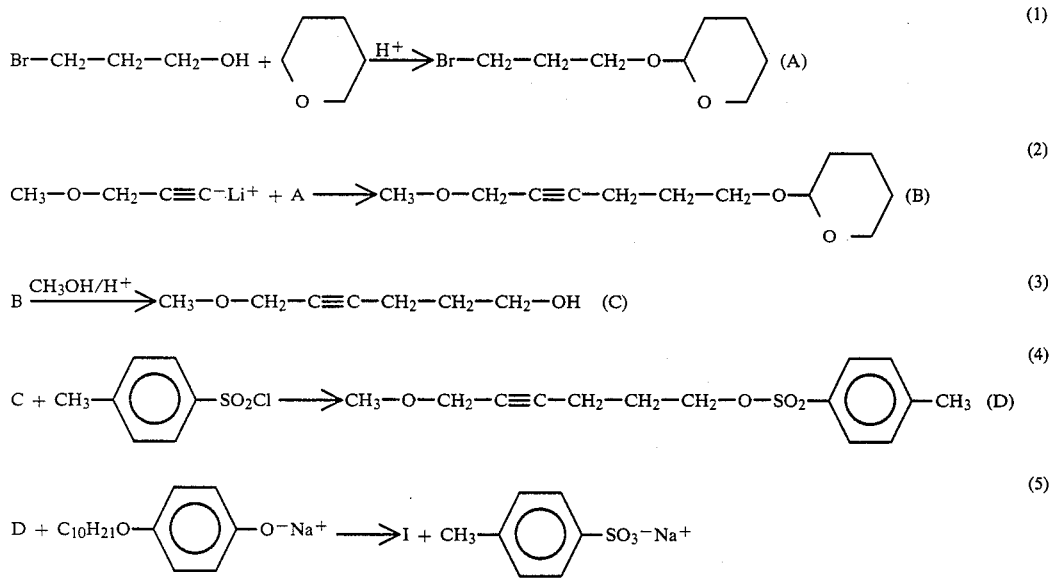

Reaction 1 of Scheme 1 consists in protecting the alcoholic function of 3-bromo-propanol in order to prepare the successive reaction.

Reaction 1 is illustrative of the preparation of the tetrahydropyranyl derivative, but it is possible to protect the hydroxy group also according to other variants known in organic chemistry.

Reaction 2 represents the reaction between the lithium salt (acetylide) of methyl-propargyl-ether and the 3-bromo-propanol protected on the alcoholic functional group (A).

Acetylide is generally prepared in situ by reacting methyl-propargyl-ether with lithium-butyl.

Then it is necessary to free the product obtained by reaction 2 (B) from the protective group on the terminal hydroxy group (reaction 3). The resulting alcohol (C) is then converted into the corresponding p.toluene-sulphonic ester by reaction with p.toluene-sulphonic acid chloride in order to transform the terminal hydroxyl group into a group more reactive as "leaving group" (reaction 4).

p.toluene-sulphonate (D) is then condensed with the sodium salt of 4-decyloxy-phenol according to reaction 5.

The process described hereinabove exhibits several drawbacks which reduce its validity from an industrial viewpoint. These drawbacks depend on the necessity of carrying out necessary but expensive operations, such as the protection of the hydroxy group (reaction 1), removal of the protective group from hydroxy group (reaction 3) and functionalizing the hydroxy group as p.toluene-sulphonate (reaction 4).

These and other reactions require the use of expensive and dangerous reagents such as lithium-butyl and p.toluene-sulphonic acid chloride, which are practically impossible to recover.

Furthermore, in connection with the fact that the process comprises a number of steps and that for some of such steps it is necessary to isolate the intermediates obtained, the process yields are not particularly high.

THE PRESENT INVENTION

We have now found a process, which is the object of the present invention, for the synthesis of compound I consisting in reacting the sodium salt of methyl-propargyl-ether (acetylide) with 1-bromo-3-chloro-propane to obtain the compound of formula: $CH_3-O-CH_2-C\equiv C-CH_2-CH_2-CH_2-Cl$ and in reacting the latter compound with the sodium salt of 4-decyloxy-phenol, according to the reactions shown in following scheme 2.

Scheme 2

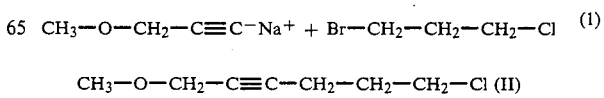

-continued
Scheme 2

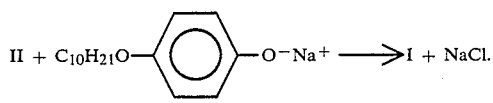
(2)

Methyl-propargyl-ether and 1-bromo-3-chloro-propane are known compounds commercially available.

Reaction 1 is accomplished according to the following operative modalities. Methyl-propargyl-ether is added dropwise to a sodium amide (NaNH$_2$) suspension in liquid ammonia, maintained under stirring at a temperature lower than or equal to −33° C. and in a nitrogen atomsphere. After about 30 minutes, a solution of 1-bromo-3-chloro-propane in anhydrous tetrahydrofuran (THF) is added dropwise in a way to prevent the temperature from rising above −33° C.

At the conclusion of the addition, the temperature is allowed to spontaneously rise and the evolving ammonia is collected and recycled or removed by bubbling in acid water.

When the temperature of the mixture is above 0° C., water is added and the mixture is worked up according to usual techniques to isolate compound II, which is employable as rough product in the successive reaction (reaction 2, scheme 2) or is purified by distillation.

The suspension of NaNH$_2$ in liquid ammonia can be also prepared in the same reaction vessel by reacting metal sodium with ammonia in the presence of ferric nitrate [Fe(NO$_3$)$_3$] as a catalyst.

The concentration of the sodium salt of methyl-propargyl-ether in liquid ammonia is not critical; for practical reasons it is preferred to use rather concentrated solutions, for example 1 molar solution.

In accordance with the reaction stoichiometry, the sodium salt of methyl-propargyl-ether and 1-bromo-3-chloro-propane are reacted in substantially equimolecular amounts.

A slight excess of sodium salt of methyl-propargyl-ether can be optionally employed.

Also the reaction for preparing the abovesaid sodium salt is carried out by using substantially equimolecular amounts of sodium amide and of methyl-propargyl-ether.

The amount of THF to be employed is not critical; generally it is preferable to utilize an amount thereof ranging from 20 to 80% of the liquid ammonia volume, and in any case a volume of THF not lower than the 1-bromo-3-chloro-propane volume.

Reaction 2 is conducted by adding to a solution of sodium salt of 4-decyloxy-phenol in a proper inert polar solvent, a substantially equimolecular amount or a slight excess of compound II optionally dissolved in a proper solvent.

The reaction can be carried out at room temperature, but a slight heating (60°-70° C.) facilitates the course thereof. After about 4-6 hours, i.e. after disappearance of the reagents (gaschromatographic analysis), the reaction mixture is treated according to conventional modalities and product I is obtained with yields higher than 90% and with a high purity degree.

The sodium salt of 4-decyloxy-phenol can be prepared in situ by reacting the corresponding phenol with sodium hydroxide in the same inert polar solvent.

As compared with the process illustrated in scheme 1, in accordance with European patent application No. 37,092, the process object of this invention offers several advantages, which can be summarized as follows:

simple feasibleness: the process forming the object of the present invention is carried out in two steps only and requires the isolation of only one intermediate (compound II) which, however, needs not necessarily to be purified; the process of scheme 1 must be carried out in five steps and requires the isolation of four intermediates (compounds A,B, C and D);

economy: the organic reagents employed in the process according to this invention directly serve to the preparation of compound I, while in the process of scheme 1 it is necessary to employ organic reagents with different purposes such as tetrahydropyranyl or equivalents thereof as protective group, and p.toluene-sulphonyl-chloride to transform the hydroxyl of compound C into a good leaving group;

better industrial suitability: the process object of the present invention, thanks to its simple feasibleness and to the fact that it comprises only two steps, requires less expensive plants and lower investment costs and can be easily converted into a continuous process.

The process according to scheme 1, as it consists of five steps and requires the isolation of four intermediates, requires more complex plants of larger dimensions, which results in higher investment costs;

less pollution problems: the waste products of the process according to the invention consist of NaBr and NaCl which do not raise problems connected with the environmental pollution as are encountered with the waste products of the process of scheme 1 (tetrahydropyrane or another protective group and sodium p.toluene-sulphonate), which, besides, are recoverable only with a too high increase in costs.

The following examples are given to better illustrate the present invention.

EXAMPLE 1

Preparation of compound
1-methoxy-6-chloro-hexyne-2

(Compound II)

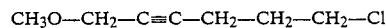

12 g (0.5 moles) of sodium and 0.4 g of Fe(NO$_3$)$_3$ were added to 500 ml of liquid ammonia kept in a nitrogen atmosphere at −33° C. An about 1 molar sodium amide suspension in liquid ammonia was obtained. To this suspension, 35 g (about 0.5 moles) of methyl-propargyl-ether (CH$_3$—O—CH$_2$—C≡CH) were gradually added while keeping the temperature below −33° C. After 30 minutes, a solution of 79 g (about 0.5 moles) of 1-bromo-3-chloro-propane (Br—CH$_2$—CH$_2$—CH$_2$—Cl) in 300 ml of anhydrous THF was added dropwise.

At the conclusion of this addition, the temperature was allowed to spontaneously rise and the ammonia to evaporate.

When the temperature reached 0°-5° C., 200 ml of water were added. The organic phase was separated and the aqueous phase was extracted with ethyl ether (1×100 ml).

The joined organic phases were dried on anhydrous Na$_2$SO$_4$ and the solvents were removed by evaporation under reduced pressure. There were obtained 40.6 g of a rough product consisting of compound II at 92% of purity (gas-chromatographic analysis) with a yield of 52%. The rough product was directly employable for the subsequent reaction (described in example 2), or it was purified by distillation under reduced pressure, collecting the fraction boiling at 55° C. at a pressure of 2 mm Hg.

$^1$H-NMR (CDCl$_3$, TMS). δ(ppm): 1.95 (m, 2H, CH$_2$—CH$_2$Cl) 2.4 (m, 2H, ≡C—CH$_2$) 3.3 (s, 3H, CH$_3$) 3.7 (t, 2H, CH$_2$—Cl) 4 (t, 2H, O—CH$_2$, J=0.2) (s=singlet, t=triplet, m=multiplet or non-resolved complex signal, J=coupling constant).

EXAMPLE 2

Preparation of compound 1-decyloxy-4-[(7-oxa-4-octynyl)-oxy]-benzene (Compound I)

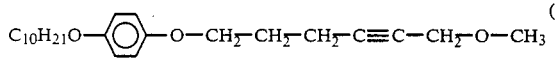
(I)

350 g (about 1.33 moles) of 4-decyloxy-phenol at 95%

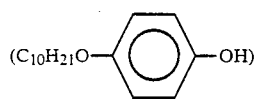

were added to a suspension of 64 g (1.6 moles) of ground NaOH in 1200 ml of DMSO, under stirring at room temperature.

The mixture was stirred for about 3 hours, whereupon 230 g (about 1.46 moles) of 1-methoxy-6-chloro-hexyne-2 (compound II) at a purity of 92% (gas-chromatographic titer) were added dropwise thereto.

The reaction mixture was heated to 60°–70° C. during 6 hours, i.e. until disappearance of the reagents (gas-chromatographic check). 5 l of water were then added, and it was extracted with about 4 liters of ethyl ether divided into a number of portions. The joined ethereal extracts were washed with 1.5 l of water. The solution was concentrated by evaporating most of the solvent, and the residue was diluted with 3 l of n.hexane.

The solution in hexane was percolated on silica gel by eluting with hexane.

The solvent was then removed by evaporation under reduced pressure and the residue was dried under high vacuum.

Thus there were obtained 468 g of compound I (melting point: 33°–34° C.) which exhibited spectroscopic characteristics analogous with those described in European patent application No. 37, 092 and a gas-chromatographic titer higher than 96% (yield calculated on introduced 4-decyloxy-phenol=93.8%).

What we claim is:

1. A process for preparing compound 1-decyloxy-4-[(7-oxa-4-octynyl)-oxy]-benzene of formula:

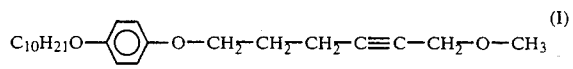
(I)

characterized in that the sodium salt of methyl-propargyl-ether of formula:

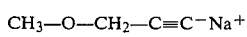

CH$_3$—O—CH$_2$—C≡C$^-$Na$^+$ is reacted in liquid ammonia at a temperature of −33° C. and in a nitrogen atmosphere with a substantially equimolecular amount of 1-bromo-3-chloro-propane in anhydrous tetrahydrofuran, thus obtaining compound 1-methoxy-6-chloro-hexyne-2 of formula:

CH$_3$O—CH$_2$—C≡C—CH$_2$—CH$_2$—CH$_2$—Cl  (II)

which is reacted in an inert polar solvent and at a temperature ranging from room temperature to 70° C. with a substantially equimolecular amount of sodium salt of 4-decyloxy-phenol of formula:

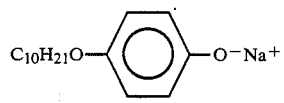

2. A process according to claim 1, characterized in that the sodium salt of methyl-propargyl-ether is in an about 1 molar concentration in liquid ammonia.

3. A process according to claim 1, characterized in that the sodium salt of methyl-propargyl-ether is prepared in situ by reacting the corresponding ether with sodium amide (NaNH$_2$) in liquid ammonia.

4. A process according to claim 1, which comprises suspending the sodium salt of methyl-propargyl-ether in liquid ammonia, adding to the suspension, while maintaining it at about −33° C. and in a nitrogen atmosphere, a solution of 1-bromo-3-chloro-propane in anhydrous tetrahydrofuran, allowing the ammonia to evaporate, isolating the resulting 1-methoxy-6-chloro-hexyne-2, and adding it to a solution of the sodium salt of 4-decyloxy-phenol in a polar solvent.

5. The process of claim 4 in which the sodium salt of 4-decyloxy-phenol is prepared in situ by reacting the corresponding phenol with sodium hydroxide in said polar solvent.

* * * * *